(12) United States Patent
Gregson et al.

(10) Patent No.: US 12,315,142 B2
(45) Date of Patent: May 27, 2025

(54) AUTOMATED CLUSTERING OF ANOMALOUS HISTOPATHOLOGY TISSUE SAMPLES

(71) Applicant: Deciphex, Glasnevin (IE)

(72) Inventors: Mark Gregson, Dublin (IE); Hammad A. Qureshi, Dublin (IE)

(73) Assignee: DECIPHEX, Dublin (IE)

( * ) Notice: Subject to any disclaimer, the term of this patent is extended or adjusted under 35 U.S.C. 154(b) by 982 days.

(21) Appl. No.: 17/379,430

(22) Filed: Jul. 19, 2021

(65) Prior Publication Data

US 2021/0342570 A1 Nov. 4, 2021

Related U.S. Application Data

(63) Continuation-in-part of application No. 16/200,987, filed on Nov. 27, 2018, now Pat. No. 11,069,062.
(Continued)

(51) Int. Cl.
*G06N 3/045* (2023.01)
*G06F 18/231* (2023.01)
(Continued)

(52) U.S. Cl.
CPC .......... *G06T 7/0012* (2013.01); *G06F 18/231* (2023.01); *G06F 18/2411* (2023.01); *G06N 3/045* (2023.01); *G06N 3/08* (2013.01); *G06V 10/50* (2022.01); *G06V 10/764* (2022.01); *G06V 10/82* (2022.01); *G06V 20/698* (2022.01)

(58) Field of Classification Search
CPC .......... G16H 50/20; G16H 30/40; G06K 9/66; G06T 2207/10024; G06T 2207/20072; G06T 2207/20081; G06T 2207/30024; G06T 2207/20084; G06T 7/0014; G06F 18/231; G06F 18/2411; G06N 3/045; G06N 3/08; G06N 3/047; G06N 3/088;
(Continued)

(56) References Cited

U.S. PATENT DOCUMENTS

2016/0058423 A1 3/2016 Kim
2016/0232425 A1* 8/2016 Huang ................... G06F 18/253
(Continued)

FOREIGN PATENT DOCUMENTS

AU 2016201298 A1 9/2017

OTHER PUBLICATIONS

International Preliminary Report on Patentability dated Jun. 2, 2020 for International Application No. PCT/EP2018/082744.
(Continued)

*Primary Examiner* — Siamak Harandi
(74) *Attorney, Agent, or Firm* — Tarolli, Sundheim, Covell & Tummino LLP

(57) ABSTRACT

Systems and methods are provided for generating clusters of anomalous images. Histopathological samples are images at an associated imaging system to produce a plurality of images. A plurality of anomalous images are identified from the plurality of images at an anomaly detection system, having an associated latent space. The plurality of anomalous images are clustered to generate a plurality of clusters within a feature space defined by a set of classification features. The set of classification features include a feature derived from the latent space associated with the anomaly detection system.

20 Claims, 3 Drawing Sheets

Related U.S. Application Data

(60) Provisional application No. 62/590,861, filed on Nov. 27, 2017.

(51) Int. Cl.
| | |
|---|---|
| *G06F 18/2411* | (2023.01) |
| *G06N 3/08* | (2023.01) |
| *G06T 7/00* | (2017.01) |
| *G06V 10/50* | (2022.01) |
| *G06V 10/764* | (2022.01) |
| *G06V 10/82* | (2022.01) |
| *G06V 20/69* | (2022.01) |

(58) Field of Classification Search
CPC .... G06V 10/764; G06V 10/82; G06V 20/698; G06V 2201/03
USPC .......................................................... 382/128
See application file for complete search history.

(56) References Cited

U.S. PATENT DOCUMENTS

| | | |
|---|---|---|
| 2018/0130207 A1 | 5/2018 | Anderson |
| 2019/0130279 A1* | 5/2019 | Beggel .................... G06V 10/82 |
| 2020/0020098 A1* | 1/2020 | Odry ..................... G06T 7/0012 |

OTHER PUBLICATIONS

Anonymous: "Isolation Forests for Anomaly Detection Improve Fraud Detection." Oct. 31, 2016, XP055542633 https://blog.easysol.net/using-isolation-forests-anamoly-detection/.

* cited by examiner

AUTOMATED CLUSTERING OF ANOMALOUS HISTOPATHOLOGY TISSUE SAMPLES

RELATED APPLICATIONS

The present application claims priority to each of U.S. Provisional Patent Application Ser. No. 62/590,861 filed Nov. 27, 2017 entitled AUTOMATED SCREENING OF HISTOPATHOLOGY TISSUE SAMPLES VIA ANALYSIS OF A NORMAL MODEL, and U.S. patent application Ser. No. 16/200,987 filed Nov. 27, 2018 entitled AUTOMATED SCREENING OF HISTOPATHOLOGY TISSUE SAMPLES VIA ANALYSIS OF A NORMAL MODEL, the entire contents of each being incorporated herein by reference in its entirety for all purposes.

TECHNICAL FIELD

The present invention relates generally to the field of medical diagnostics, and more particularly to automated clustering of anomalous histopathology tissue samples.

BACKGROUND OF THE INVENTION

Histopathology refers to the microscopic examination of tissue in order to study the manifestations of disease. Specifically, in clinical medicine, histopathology refers to the examination of a biopsy or surgical specimen by a pathologist, after the specimen has been processed and histological sections have been placed onto glass slides. The medical diagnosis from this examination is formulated as a pathology report describing any pathological changes in the tissue. Histopathology is used in the diagnosis of a number of disorders, including cancer, drug toxicity, infectious diseases, and infarctions.

SUMMARY OF THE INVENTION

In one implementation, a method is provided for generating clusters of anomalous images. Histopathological samples are images at an associated imaging system to produce a plurality of images. A plurality of anomalous images are identified from the plurality of images at an anomaly detection system, having an associated latent space. The plurality of anomalous images are clustered to generate a plurality of clusters within a feature space defined by a set of classification features. The set of classification features include a feature derived from the latent space associated with the anomaly detection system.

In another implementation, a system includes a processor and a non-transitory computer readable medium storing executable instructions. The instructions are executable by the processor to provide an imager interface that receives histopathological samples from an associated imaging system to produce a plurality of images and an anomaly detection system, having an associated latent space, that identifies a plurality of anomalous images from the plurality of images. A clustering system clusters the plurality of anomalous images to generate a plurality of clusters within a feature space defined by a set of classification features that includes at least one feature derived from the latent space associated with the anomaly detection system.

In yet another implementation, a method is provided for generating clusters of anomalous images. A plurality of anomalous images from the plurality of images are identified at an anomaly detection system. The anomaly detection system includes an autoencoder having an associated latent space. Dimensionality reduction is applied to a first set of values extracted from the latent space and a second set of values representing a reconstruction error of the encoder to provide a set of classification features. The plurality of anomalous images are clustered to generate a plurality of clusters within a feature space defined by the set of classification features . . . .

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Systems and methods are provided for automated identification and clustering of abnormal histopathology tissue samples. The clustering can be used to categorize abnormal tissue samples, facilitating labeling of these samples. The labeled samples can be used to characterize the abnormalities and their clinical implications, as well as for labeling training samples for other expert systems. The clustering process can utilize features drawn from a latent space of an anomaly detection system used to identify the anomalous images, allowing the clustering to be performed with feature space having a reduced dimensionality. Further dimensionality reduction, for example, via uniform manifold approximation and projection (UMAP), can be applied to further reduce the feature space and improve the efficiency of the clustering process.

Figure 1:
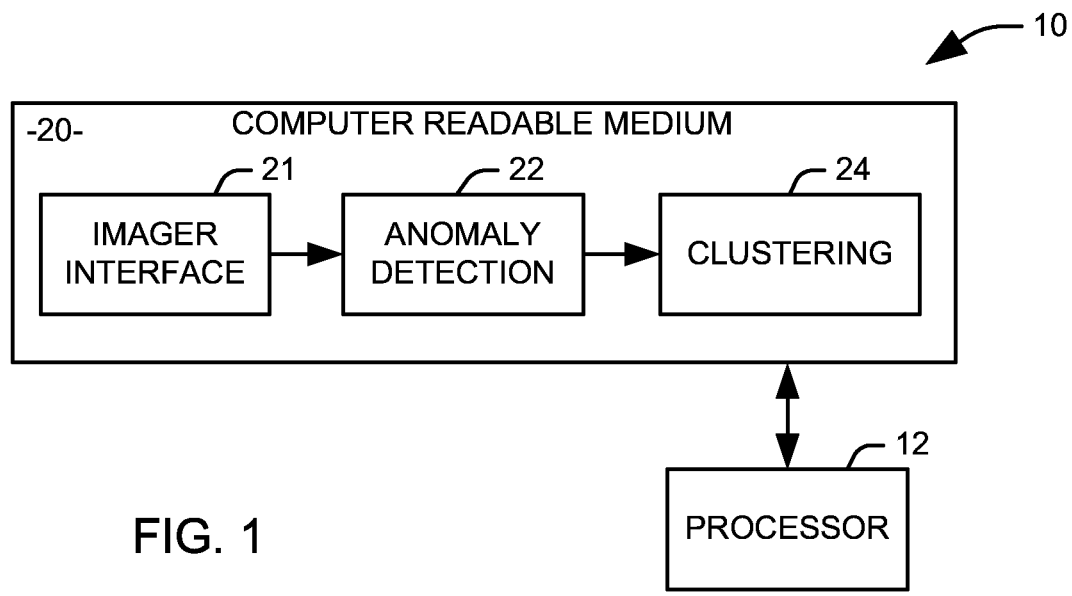
FIG. 1 illustrates a functional block diagram of a system for generating clusters of anomalous images.

FIG. 1 illustrates a functional block diagram of a system 10 for generating clusters of anomalous images. The system 10 includes a processor 12 and a non-transitory computer readable medium 20 that stores executable instructions for evaluating histopathology tissue samples. In the illustrated implementation, the non-transitory computer readable medium 20 stores an imager interface 21 that receives images of histopathological tissue samples from an associated imaging system (not shown) to produce a plurality of digital images. It will be appreciated that the histopathology tissue samples can include tissue from the gastrointestinal system, the prostate, the skin, the breast, the kidneys, the liver, the lymph nodes, and any other appropriate location in a body of a human or animal subject. Tissue can be extracted via biopsy or acquired via excision or analysis of surgical specimens. In the case of animal subjects, tissue sections can be taken during an autopsy of the animal. The non-transitory computer readable medium 20 also stores an anomaly detection system 22 trained on a plurality of training images. It will be appreciated that the training images can be acquired from stained histopathology tissue samples, for example, hematoxylin and eosin (H&E) stained or immunostained slides, which may have one or more stain normalization processes applied to standardize the images.

In practice, the images can be whole slide images, single frame capture images from a microscope mounted camera, or images taken during endoscopic procedures. The images can be brightfield, greyscale, colorimetric, or fluorescent images, and can be stored in any appropriate image format. Tissue abnormalities can include polyps, tumors, inflammation, infection sites, or other abnormal tissue within a body. In the liver, abnormalities can include infiltrate, glycogen, necrosis, vacuolation, hyperplasia, hypertrophy, fibrosis, hematopoiesis, granuloma congestion, pigment, arteritis, cholestasis, nodule, hemorrhage, and mitotic figures/regeneration. In the kidney, abnormalities can include infiltrate, necrosis, vacuolation, basophilic tubule, cast renal tubule, hyaline droplet, hyperplasia, fibrosis, hematopoiesis, degeneration/regeneration/mitotic figures, mineralization, dilation, hypoplasia, hypertrophy, pigment, nephropathy, glomerulosclerosis, cysts, congestion, and hemorrhage.

In practice, the anomaly detection system 22 can be implemented as any of a plurality of expert systems, along with appropriate logic for extracting classification features from the training images and any submitted test images. In one implementation, the extracted features can include both more traditional image processing features, such as color, texture, and gradients, as well as features derived from the latent space of an autoencoder. In one implementation, the anomaly detection system 22 is trained to represent a normal model, and to this end, each of the plurality of training images represents a tissue sample that is substantially free of abnormalities. In this implementation, no images of specific tissue pathologies or other abnormalities is necessary for the training process.

Appropriate expert systems can include, for example, density-based techniques, such as k-nearest neighbor, and local outlier factor, subspace-based and correlation-based outlier detection for high-dimensional data, single-class support vector machines, replicator neural networks, cluster analysis-based outlier detection, deviations from association rules and frequent item sets, fuzzy logic based outlier detection, ensemble techniques, isolation forest, one-class random forest, an elliptic envelope approach, for example, utilizing a covariance-weighted distance metric such as the Mahalanobis distance, and a reconstruction image difference from an autoencoder or generative adversarial network. In one implementation, multiple expert systems are utilized, with their individual outputs provided to an arbitrator to provide a deviation from normal score from the plurality of outputs.

Figure 2:
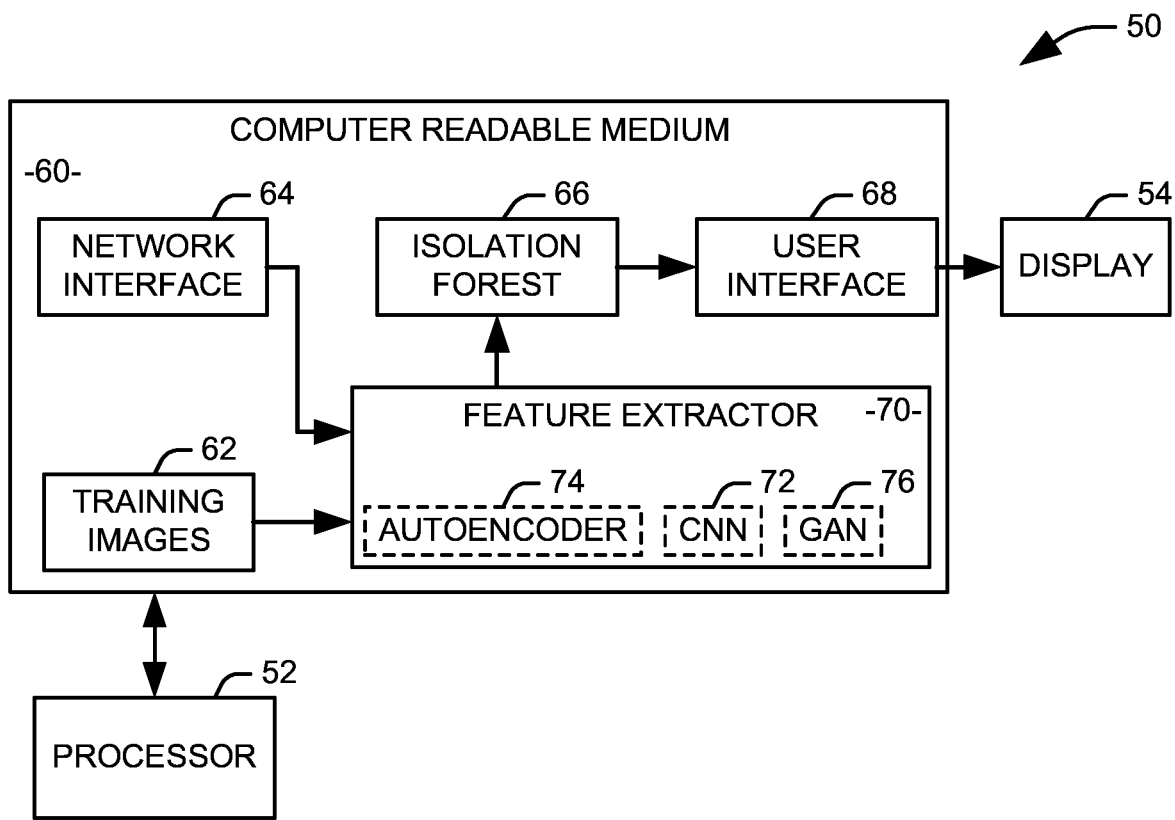
FIG. 2 illustrates an example of an anomaly detection system for screening histopathology tissue samples via a normal model that can be used with the system of FIG. 1.

FIG. 2 illustrates an example of an anomaly detection system 50 for screening histopathology tissue samples via a normal model that can be used with the system of FIG. 1. By a "normal model", it is meant that the model is generated by training an expert system from images that are substantially free of pathologies or other abnormalities. The system 50 includes a processor 52 and a non-transitory computer readable medium 60 that stores executable instructions for evaluating histopathology tissue samples. In the illustrated implementation, the non-transitory computer readable medium 60 stores a set of training images 62, each representing a tissue sample that is substantially free of abnormalities. Each of the set of training images 62 can be provided to a feature extractor 70, which extracts classification features from the training images. It will be appreciated that, instead of storing the training images 62 on the medium 60, they could instead be provided directly to the feature extractor 70 from a remote system via a network interface 64.

The feature extractor 70 can process each image to provide a plurality of feature values for each image. In the illustrated implementation, this can include both global features of the image as well as regional or pixel-level features extracted from the image. In the illustrated implementation, the extracted features can include a first set of features generated from histograms of various image processing metrics for each of a plurality of regions, the metrics including values representing color, texture, and gradients within each region. Specifically, one set of features can be generated from multi-scale histograms of color and texture features. Another set of features can be generated via a dense Speeded-Up Robust Features (SURF) feature detection process.

Additional features can be generated from latent features generated by other expert systems. In the illustrated implementation, the features can include latent vectors generated by a convolutional neural network 72 (CNN), an autoencoder 74, such as a variational autoencoder, and a generative adversarial network (GAN) 76. It will be appreciated that each of the convolutional neural network 72, the autoencoder 74, and the generative adversarial network 76 are trained on the set of training images 62. The convolutional neural network 72, in general terms, is a neural network that has one or more convolutional layers within the hidden layers that learn a linear filter that can extract meaningful structure from an input image. As a result, one or more hidden layers of the convolutional neural network 72 can be utilized as classification features.

The autoencoder 74 is an unsupervised learning algorithm that applies backpropagation to an artificial neural network, with the target values to be equal to the inputs. By restricting the number and size of the hidden layers in the neural network, as well as penalizing neuron activation, the neural network defines a compressed, lower dimensional representation of the image in the form of latent variables, which can be applied as features for anomaly detection. In one implementation, the autoencoder 74 is a variational autoencoder, that works similarly, but restricts the distribution of the latent variables according to variational Bayesian models.

The generative adversarial network 76 uses two neural networks, a first of which generates candidates and the second of which evaluates the candidates. Typically, the generative network learns to map from a latent space to a particular data distribution of interest, taken from a training set, while the discriminative network discriminates between instances from the true data distribution and candidates produced by the generator. The generative network's training objective is to increase the error rate of the discriminative network by producing novel synthesized instances that appear to have come from the true data distribution. As the quality of the synthetic images at the generative network and the discrimination at the discriminative network increase, the features formed in the hidden layers of these networks become increasingly representative of the original data set, making them potentially useful features for defining the normal model.

The extracted features are then provided to an isolation forest algorithm 66 as a feature vector representing the test image. The isolation forest algorithm 66 isolates a given feature vector in feature space by randomly selecting a feature and then randomly selecting a split value between the maximum and minimum values of the selected feature. This is continued until the feature vector is separated from the other feature vectors in the training set or until another termination condition is reached. These separations are represented as isolation trees, or random decision trees, and a score can be calculated as the path length along the tree to isolate the observation. To avoid issues due to the randomness of the tree algorithm, the process is repeated several times, and the average path length is calculated and normalized. It will be appreciated that the isolation forest algorithm 66 is trained on the training set 62 to provide a normal model, and thus the other feature vectors in the isolation forest algorithm represent tissue samples are free from abnormality. Accordingly, test images that differ significantly from normal images should be isolated, on average, fairly quickly, while test images containing abnormalities should be isolated more rapidly. Accordingly, the average path length represents a deviation from normal for the test image, and either the average path length or a function of the average path length can be reported to a user via a user interface 68 as the deviation from normal score at an associated display 54.

Returning to FIG. 1, the image interface 21 receives test images from a stored set of test images, each representing a tissue sample for analysis, and provides the test image to the anomaly detection system 22. The anomaly detection system 22 evaluates the test image and generates a set of anomalous images from the set of test images. The set of anomalous images are provided to a clustering system 24 that clusters the plurality of anomalous images to generate a plurality of clusters within a defined feature space. In accordance with an aspect of the present invention, the feature space can be defined by a set of classification features that includes a feature derived from the latent space associated with the anomaly detection system 22. For example, the anomaly detection system 22 can be implemented as any of a convolutional neural network, an autoencoder, a generative adversarial network, or another neural network system, and one or more features can be drawn from one or more hidden layers of the network. The clusters of anomalous images can then be displayed to a user or stored on the non-transitory computer readable medium 20.

Figure 3:
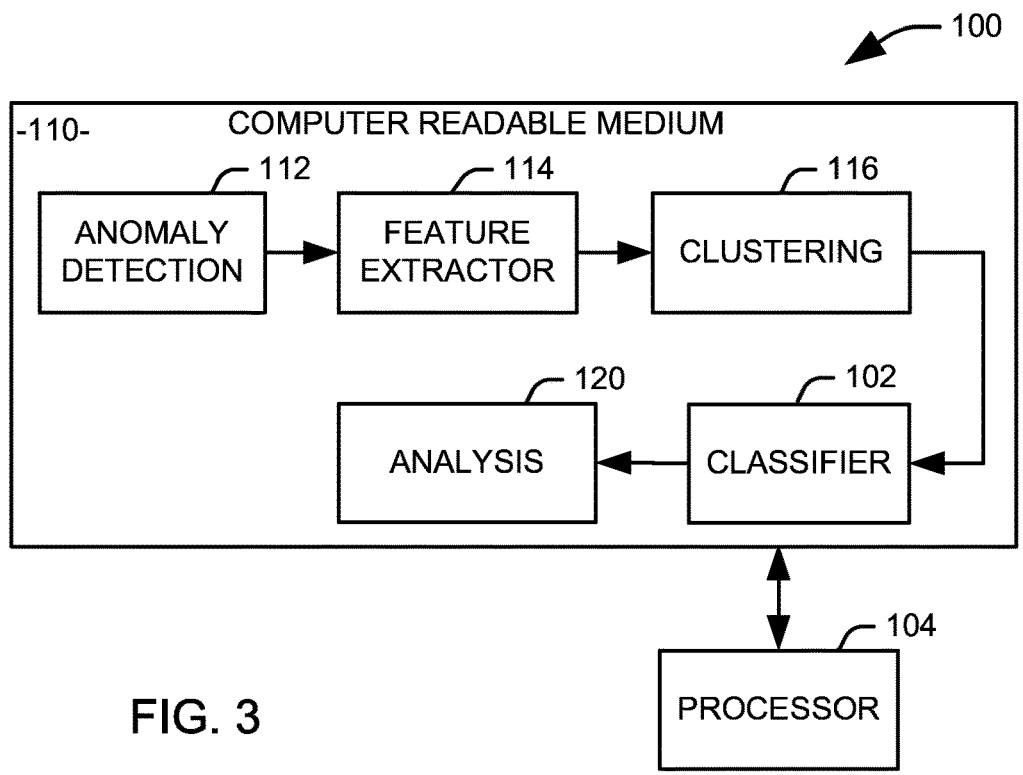
FIG. 3 illustrates a system for training a machine learning system to identify abnormalities in tissue in accordance with an aspect of the present invention.

FIG. 3 illustrates a system 100 for training a classifier system 102 to identify abnormalities in tissue in accordance with an aspect of the present invention. The system 100 includes a processor 104 and a non-transitory computer readable medium 110 that stores executable instructions for evaluating histopathology tissue samples. In the illustrated implementation, the executable instructions include an anomaly detection system 112 that identifies a plurality of anomalous images from the plurality of images. In one implementation, the anomaly detection system 112 is implemented as an autoencoder. In another implementation, the anomaly detection system 112 is implemented as a generative adversarial network. In a further embodiment, the anomaly detection system 112 is implemented as a convolutional neural network.

The anomalous images identified by the anomaly detection system 112 are provided to a feature extractor 114 that extracts a set of classification features from each of the plurality of training images. In accordance with an aspect of the present invention, the set of classification features includes at least one feature derived from a latent space of the anomaly detection system 112. For example, values from one or more hidden layers of the anomaly detection system 112 can be extracted at the feature extractor 114 for each image. It will be appreciated that additional values can also be included in the set of classification features extracted from each image, and in one implementation, in which the anomaly detection system 112 is an autoencoder, a plurality of features can be extracted from a reconstruction error of the autoencoder. Additionally or alternatively, the feature extractor 114 can apply dimensionality reduction to the values extracted from the latent space and any additional values, such as any values representing a reconstruction error, to provide the set of classification features. It will be appreciated that any appropriate dimensionality reduction process can be used, including, but not limited to, principle component analysis, including graph-based and kernel approaches, non-negative matrix factorization, linear discriminate analysis, generalized discriminant analysis, T-distributed stochastic neighbor embedding, and uniform manifold approximation and projection (UMAP). In one implementation, UMAP is applied to a set of features derived from the reconstruction error of an autoencoder associated with the anomaly detection system 112 and values drawn from a latent space of the autoencoder.

The extracted features are provided to a clustering system 116 that clusters the plurality of anomalous images to generate a plurality of clusters within a feature space defined by a set of classification features. In one example, the clustering system 116 applies a hierarchical clustering algorithm to the plurality of anomalous images. It will be appreciated that the clusters can represent different sorts of anomalies as well as false positives, and that the plurality of clusters can include both clusters of anomalous images and clusters of normal images. Alternatively or additionally, a set of normal images can be added to the anomalous images to ensure that at least some normal samples are represented in the clustering process.

Once the plurality of anomalous images 116 have been divided into the plurality of clusters, at least a portion of the images can be used to train the classifier system 102, with each image labeled with the cluster to which is was assigned by the clustering system 102. Accordingly, the classification system 102 can be trained to assign a cluster membership to new samples provided to the system or to assign a continuous or categorical parameter to the image based upon its projected cluster membership or proximity to a given cluster in the defined feature space. For example, it will be appreciated that multiple of the plurality of clusters may represent a class of clinical interest, and that an assigned categorical may be the same for any of the multiple clusters. In one implementation, the classification system 102 can be implemented as a convolutional neural network. In this implementation, or other implementations using artificial neural networks, the system 100 can further include an analysis component 120 that generates one or both of a class activation map and a set of integrated gradients for at least one latent layer of the artificial neural network. From the class activation map and/or gradients, the activation map can provide classification maps based upon probabilities of various classes, for example, normal and anomalous classification.

The clinical parameter provided by the classification system 102 can be a continuous or categorical value representing the health or well-being of a patient or subject based on the appearance of tissue. In one implementation, the image provided to the classification system 102 is a tissue sample is obtained from a patient (e.g., via a biopsy) and the clinical parameter is used to diagnose or monitor a medical condition in the patient. In another implementation, a therapeutic (e.g., a drug) can be administered to an animal subject for evaluation of the effects of the therapeutic on one or more organs of the subject. In yet another implementation, a therapeutic to a subject associated with the tissue sample after a first set of tissue samples has been evaluated. A second tissue sample can be extracted, analyzed, and compared to the first sample to determine an efficacy of the therapeutic in treating an existing condition.

Figure 4:
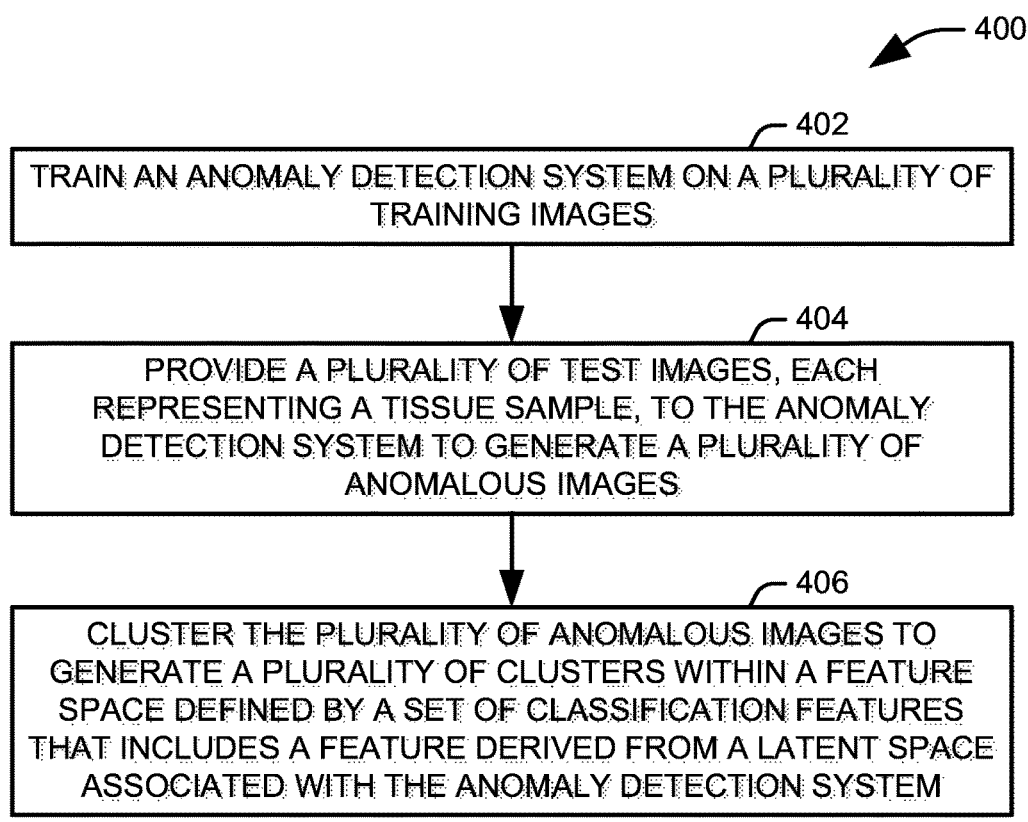
FIG. 4 illustrates one example of a method for generating clusters of anomalous images.
Figure 5:
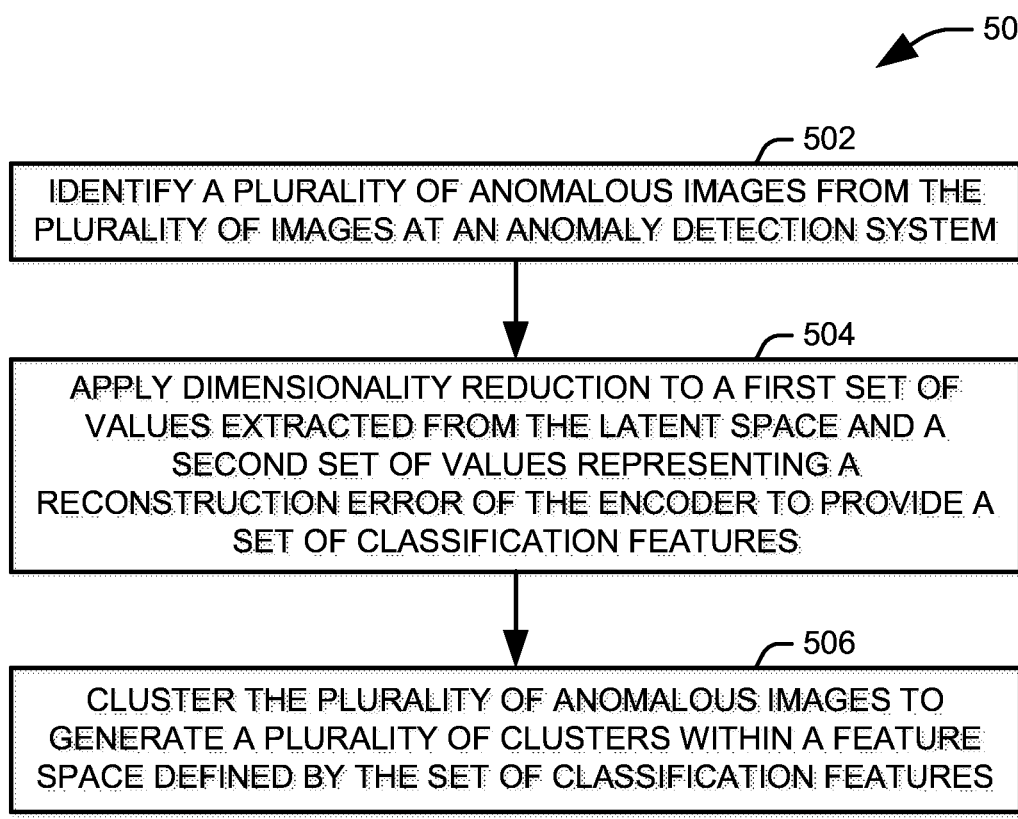
FIG. 5 illustrates another example of a method for generating clusters of anomalous images.

In view of the foregoing structural and functional features described above, a method in accordance with various aspects of the present invention will be better appreciated with reference to FIGS. 4 and 5. While, for purposes of simplicity of explanation, the methods of FIGS. 4 and 5 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention.

FIG. 4 illustrates one example of a method 400 for generating clusters of anomalous images. At 402, an anomaly detection system is trained on a plurality of training images. In one example, each of the plurality of training images represents a tissue sample that is substantially free of abnormalities, such that the anomaly detection system is trained to represent a normal model, in which only tissue samples substantially free of abnormality are represented. At 404, a plurality of test images, each representing a tissue sample, are provided to the anomaly detection system to generate a plurality of anomalous images. In one example, the anomaly detection system can represent the test image as a vector of features, including features derived from color, texture, and gradient values extracted from the image as well as features derived from the latent space of an expert system applied to the image, such as a convolutional neural network, autoencoder, or generative adversarial network. In one example, using a normal model as described above, a deviation from normal score can be generated for at least a portion of the test image using one or more anomaly detection algorithms. The deviation from normal score represents a degree of abnormality in the tissue sample represented by the test image, specifically a degree to which the test image deviates from a normal model represented by the anomaly detection system. Specifically, a first set of clusters, representing different types of normal tissues, can be generated, and the plurality of images can be provided to the anomaly detection samples, and the plurality of anomalous images can be identified according to a distance of the image from the normal clusters.

At 406, the plurality of anomalous images are clustered to generate a plurality of clusters within a feature space defined by a set of classification features. The set of classification features includes a feature derived from the latent space associated with the anomaly detection system. In the example using the normal model described above, the plurality of anomalous images can be grouped into clusters at least partially according to the distance of each of the anomalous images from the first set of clusters and the similarity among the anomalous images. In another implementation, in which the anomaly detection system is implemented as a convolutional neural network, the set of classification features can include a set of features derived from latent vectors generated by the convolutional neural network. In a further implementation, in which the anomaly detection system is implemented as a generative adversarial network, a plurality of features can be derived from a set of values in a hidden layer of the generative adversarial network for each of the plurality of training images.

In another implementation, in which the anomaly detection system is implemented using an autoencoder, a plurality of features can be extracted from each of the plurality of training images that are derived from a reconstruction error of the autoencoder, and these values can be used in addition to any values derived from the latent space of the autoencoder. Dimensionality reduction, such as uniform manifold approximation and projection, can be applied to the values extracted from the latent space and the representing the reconstruction error to reduce the complexity of the feature space used for the clustering process. In one example, a hierarchical clustering algorithm is applied to the plurality of anomalous images. It will be appreciated that, either due to false positives in the anomaly detection or the deliberate supplement of the images provided to the clustering system, the plurality of clusters can include clusters of anomalous images and clusters of normal images.

The clusters of images can then be provided to a user via a user interface, stored in a non-transitory computer readable medium, and/or provided as training samples to a classifier system. In one implementation, sets of the plurality of anomalous images can be labeled according to their association with the plurality of clusters and a classifier on at least a portion of the sets of the plurality of anomalous images. In one example, the class represented by each of the plurality of clusters is determined to be, for example, by a human expert, either a normal class and an anomalous class, such that the classifier is trained to distinguish between normal and anomalous images. When an artificial neural network classifier, such as a convolutional neural network, is used, the trained network can be evaluated to determine the portions of the image and the various features that were important in identifying anomalous images. For example, one or both of a class activation map and a set of integrated gradients can be generated for at least one latent layer of the artificial neural network, and classification maps based upon probabilities of normal and anomalous classification can be generated accordingly.

FIG. 5 illustrates another example of a method 500 for generating clusters of anomalous images. At 502, a plurality of anomalous images from the plurality of images are identified at an anomaly detection system. The anomaly detection system includes an autoencoder having an associated latent space. At 504, dimensionality reduction is applied to a first set of values extracted from the latent space and a second set of values representing a reconstruction error of the encoder to provide a set of classification features. In one implementation, the dimensionality reduction is applied using uniform manifold approximation and projection. At 506, the plurality of anomalous images are clustered to generate a plurality of clusters within a feature space defined by the set of classification features. The clustered images can be labeled in accordance with their associated clusters and used to train an associated machine learning system.

Figure 6:
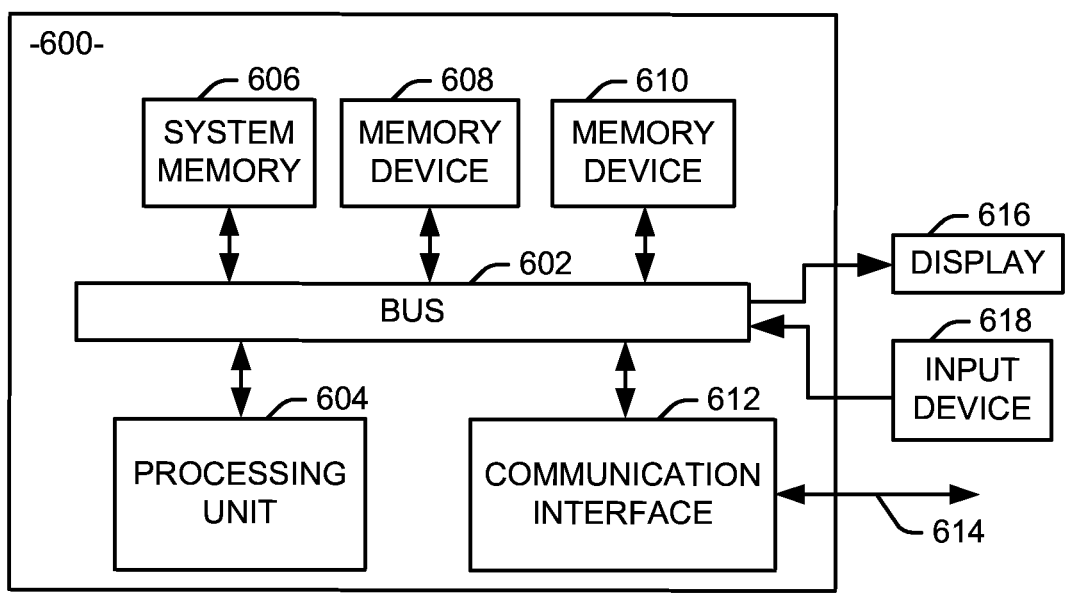
FIG. 6 is a schematic block diagram illustrating an exemplary system of hardware components capable of implementing examples of the systems and methods disclosed herein.

FIG. 6 is a schematic block diagram illustrating an exemplary system 600 of hardware components capable of implementing examples of the systems and methods disclosed in FIGS. 1-5, such as the tissue screening system illustrated in FIGS. 1-3. The system 600 can include various systems and subsystems. The system 600 can be a personal computer, a laptop computer, a workstation, a computer system, an appliance, an application-specific integrated circuit (ASIC), a server, a server blade center, a server farm, etc.

The system 600 can includes a system bus 602, a processing unit 604, a system memory 606, memory devices 608 and 610, a communication interface 612 (e.g., a network interface), a communication link 614, a display 616 (e.g., a video screen), and an input device 618 (e.g., a keyboard and/or a mouse). The system bus 602 can be in communication with the processing unit 604 and the system memory 606. The additional memory devices 608 and 610, such as a hard disk drive, server, stand-alone database, or other non-volatile memory, can also be in communication with the system bus 602. The system bus 602 interconnects the processing unit 604, the memory devices 606-610, the communication interface 612, the display 616, and the input device 618. In some examples, the system bus 602 also interconnects an additional port (not shown), such as a universal serial bus (USB) port.

The processing unit 604 can be a computing device and can include an application-specific integrated circuit (ASIC). The processing unit 604 executes a set of instructions to implement the operations of examples disclosed herein. The processing unit can include a processing core.

The additional memory devices 606, 608, and 610 can store data, programs, instructions, database queries in text or compiled form, and any other information that can be needed to operate a computer. The memories 606, 608 and 610 can be implemented as computer-readable media (integrated or removable) such as a memory card, disk drive, compact disk (CD), or server accessible over a network. In certain examples, the memories 606, 608 and 610 can comprise text, images, video, and/or audio, portions of which can be available in formats comprehensible to human beings. Additionally or alternatively, the system 600 can access an external data source or query source through the communication interface 612, which can communicate with the system bus 602 and the communication link 614.

In operation, the system 600 can be used to implement one or more parts of a system in accordance with the present invention. Computer executable logic for implementing the system resides on one or more of the system memory 606, and the memory devices 608, 610 in accordance with certain examples. The processing unit 604 executes one or more computer executable instructions originating from the system memory 606 and the memory devices 608 and 610. The term "computer readable medium" as used herein refers to any medium that participates in providing instructions to the processing unit 604 for execution, and it will be appreciated that a computer readable medium can include multiple computer readable media each operatively connected to the processing unit.

Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof. In one example, the systems of FIGS. 1-3 can be implemented on one or more cloud servers and can be configured to receive images for analysis and clustering from one or more client systems.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to, portable or fixed storage devices, optical storage devices, wireless channels, and/or various other storage mediums capable of storing that contain or carry instruction(s) and/or data.

From the above description of the invention, those skilled in the art will perceive improvements, changes, and modifications. Such improvements, changes, and modifications within the skill of the art are intended to be covered by the appended claims.

Having described the invention, We claim:

1. A method comprising:
imaging histopathological samples at an associated imaging system to produce a plurality of images;
identifying a plurality of anomalous images from the plurality of images at an anomaly detection system, the anomaly detection system having an associated latent space; and
clustering the plurality of anomalous images to generate a plurality of clusters within a feature space defined by a set of classification features, the set of classification features comprising a feature derived from the latent space associated with the anomaly detection system.

2. The method of claim 1, wherein the anomaly detection system is an autoencoder and the method further comprises extracting a plurality of features from each of the plurality of images that are derived from a reconstruction error of the autoencoder, the set of classification features comprising the plurality of features.

3. The method of claim 2, wherein extracting the plurality of features from each of the plurality of images comprises applying dimensionality reduction to a first set of values extracted from the latent space and a second set of values representing the reconstruction error to provide the set of classification features.

4. The method of claim 3, wherein applying dimensional reduction to the first set of values and the second set of values comprises applying uniform manifold approximation and projection to the first set of values and the second set of values.

5. The method of claim 1, wherein clustering the plurality of anomalous images comprises applying a hierarchical clustering algorithm to the plurality of anomalous images, the plurality of clusters comprising at least one cluster of anomalous images and at least one cluster of normal images.

6. The method of claim 1, wherein identifying the plurality of anomalous images from the plurality of images at the anomaly detection system comprises training the anomaly detection system on a plurality of training images, each of the plurality of training images representing a tissue sample that is substantially free of abnormalities, generating a first set of clusters representing different types of normal tissues, providing the plurality of images to the anomaly detection system, and identifying each of the plurality of anomalous images according to a distance of the image from the normal clusters, and the method further comprises grouping the plurality of anomalous images into clusters based upon the distance of each of the anomalous images from the first set of clusters and the similarity among the anomalous images.

7. The method of claim 1, wherein the anomaly detection system is implemented as a convolutional neural network, and the set of classification features comprising a set of features derived from latent vectors generated by the convolutional neural network.

8. The method of claim 1, further comprising labelling respective sets of the plurality of anomalous images associated with the plurality of clusters with a class represented by the cluster with which a set of the plurality of anomalous images is associated and training a classifier on at least a portion of the sets of the plurality of anomalous images.

9. The method of claim 8, wherein the class represented by each of the plurality of clusters is one of a normal class and an anomalous class, such that the classifier is trained to distinguish between normal and anomalous images.

10. The method of claim 8, wherein the classifier is a convolutional neural network.

11. The method of claim 10, further comprising generating one of a class activation map and a set of integrated gradients for at least one latent layer of the convolutional neural network and generating classification maps based upon probabilities of normal and anomalous classification from the one of the class activation map and the set of integrated gradients.

12. The method of claim 1, wherein the anomaly detection system is a generative adversarial network and the method further comprises extracting a plurality of features that are derived from a set of values in a hidden layer of the generative adversarial network from each of the plurality of images.

13. A system comprising:
a processor; and
a non-transitory computer readable medium storing executable instructions comprising:
an imager interface that receives histopathological samples from an associated imaging system to produce a plurality of images;
an anomaly detection system, having an associated latent space, that identifies a plurality of anomalous images from the plurality of images; and
a clustering system that clusters the plurality of anomalous images to generate a plurality of clusters within a feature space defined by a set of classification features that includes a feature derived from the latent space associated with the anomaly detection system.

14. The system of claim 13, wherein the anomaly detection system is an autoencoder and the system further comprises a feature extractor that extracts a plurality of features for the set of classification features from each of the plurality of images from a reconstruction error of the autoencoder.

15. The system of claim 14, wherein the feature extractor applies dimensionality reduction to a first set of values extracted from the latent space and a second set of values representing the reconstruction error to provide the set of classification features.

16. The system of claim 13, wherein the clustering system applies a hierarchical clustering algorithm to the plurality of anomalous images, the plurality of clusters comprising at least one cluster of anomalous images and at least one cluster of normal images.

17. The system of claim 13, further comprising a classifier system trained on at least a portion of the plurality of anomalous images, each of the plurality of anomalous images having a class membership associated with a cluster of the plurality of clusters to which the anomalous images is associated.

18. The system of claim 17, wherein the classifier is a convolutional neural network, the system further comprising an analysis component that generates one of a class activation map and a set of integrated gradients for at least one latent layer of the convolutional neural network and provides classification maps based upon probabilities of normal and anomalous classification from the one of the class activation map and the set of integrated gradients.

19. The system of claim 13, wherein the anomaly detection system is a generative adversarial network, and the set of classification features includes a plurality of features that are derived from a set of values in a hidden layer of the generative adversarial network from each of the plurality of images.

20. A method comprising:
   imaging histopathological samples at an associated imaging system to produce a plurality of images;
   identifying a plurality of anomalous images from the plurality of images at an anomaly detection system comprising an autoencoder, the autoencoder having an associated latent space;
   clustering the plurality of anomalous images to generate a plurality of clusters within a feature space defined by a set of classification features, the set of classification features comprising a feature derived from the latent space associated with the autoencoder.

* * * * *